United States Patent
Hull et al.

(10) Patent No.: US 10,871,061 B2
(45) Date of Patent: Dec. 22, 2020

(54) TREATMENT OF KEROGEN IN SUBTERRANEAN ZONES

(71) Applicant: Saudi Arabian Oil Company, Dhahran (SA)

(72) Inventors: Katherine Leigh Hull, Houston, TX (US); Younane N. Abousleiman, Norman, OK (US); David Jacobi, Spring, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/866,933

(22) Filed: Jan. 10, 2018

(65) Prior Publication Data
US 2019/0211658 A1    Jul. 11, 2019

(51) Int. Cl.
| | |
|---|---|
| *E21B 43/267* | (2006.01) |
| *C08L 33/26* | (2006.01) |
| *C01D 3/10* | (2006.01) |
| *C01B 11/20* | (2006.01) |
| *C07C 211/62* | (2006.01) |
| *C09K 8/03* | (2006.01) |
| *C09K 8/504* | (2006.01) |
| *C09K 8/66* | (2006.01) |

(52) U.S. Cl.
CPC ............ *E21B 43/267* (2013.01); *C01B 11/20* (2013.01); *C01D 3/10* (2013.01); *C07C 211/62* (2013.01); *C08L 33/26* (2013.01); *C09K 8/032* (2013.01); *C09K 8/5045* (2013.01); *C09K 8/665* (2013.01); *C09K 2208/28* (2013.01)

(58) Field of Classification Search
None
See application file for complete search history.

(56) References Cited

U.S. PATENT DOCUMENTS

| | | | | |
|---|---|---|---|---|
| 5,759,964 | A * | 6/1998 | Shuchart | C09K 8/08 507/209 |
| 6,749,022 | B1 | 6/2004 | Fredd | |
| 8,701,788 | B2 | 4/2014 | Wigand et al. | |
| 8,839,860 | B2 | 9/2014 | Wigand et al. | |
| 8,851,177 | B2 | 10/2014 | Wigand | |
| 8,936,089 | B2 | 1/2015 | Wigand | |
| 2007/0298979 | A1 * | 12/2007 | Perry | C09K 8/68 507/269 |
| 2008/0006410 | A1 | 1/2008 | Looney et al. | |

(Continued)

FOREIGN PATENT DOCUMENTS

WO      2012171857      12/2012

OTHER PUBLICATIONS

Siskin et al., "Reactivity of organic compounds in hot water: geochemical and technological implications," Science, Oct. 11, 1991, 8 pages.

(Continued)

*Primary Examiner* — Andrew Sue-Ako
(74) *Attorney, Agent, or Firm* — Fish & Richardson P.C.

(57) ABSTRACT

Technologies relating to increasing hydraulic fracturing efficiencies in subterranean zones by degrading organic matter, such as kerogen, are described. A method for treating kerogen in a subterranean zone includes placing a composition in the subterranean zone, and the composition includes an oxidizer including sodium bromate and an additive including a tetrasubstituted ammonium salt.

16 Claims, 2 Drawing Sheets

(56) References Cited

U.S. PATENT DOCUMENTS

| | | | |
|---|---|---|---|
| 2009/0145607 A1* | 6/2009 | Li | C09K 8/685 166/308.5 |
| 2010/0323933 A1* | 12/2010 | Fuller | C09K 8/528 507/261 |
| 2011/0259588 A1* | 10/2011 | Ali | C09K 8/665 166/280.2 |
| 2013/0161002 A1 | 6/2013 | Wigand | |
| 2014/0116710 A1 | 5/2014 | Naser-El-Din et al. | |
| 2014/0251605 A1* | 9/2014 | Hera | B01D 19/0404 166/265 |
| 2015/0075782 A1* | 3/2015 | Sharma | E21B 43/26 166/250.1 |
| 2017/0066959 A1 | 3/2017 | Hull et al. | |
| 2017/0370197 A1 | 12/2017 | Han et al. | |

OTHER PUBLICATIONS

'Glossary.oilfield.slb.com' [online], "Oilfield Glossary: fluid-friction reducer," available on or before Jun. 15, 2017, retrieved from URL< http://www.glossary.oilfield.slb.com/Terms/f/fluid-friction_reducer.aspx>, 1 page.

International Search Report and Written Opinion issued in International Application No. PCT/US2019/013003 dated Apr. 2, 2019, 12 pages.

GCC Examination Report in GCC Appln. No. GC 2019-36817, dated May 17, 2020, 4 pages.

\* cited by examiner

TREATMENT OF KEROGEN IN SUBTERRANEAN ZONES

TECHNICAL FIELD

This specification relates to treating subterranean zones for enhancing hydrocarbon recovery.

BACKGROUND

Hydraulic fracturing is a process of stimulating a well through one or more fractured rock formations. The process involves high-pressure injection of a fracturing fluid into a wellbore to create fractures, so that fluids can flow more freely through the rock formation. Hydraulic fracturing can increase the mobility of trapped hydrocarbons and therefore increase recovery of hydrocarbons from a reservoir. Fracturing fluid injection can continue until the formed fractures are wide enough to accept propping agents, which keep the formed fractures propped open after the injection ceases. There are challenges in hydraulic fracturing caused by wide variability of the propagation of the fractures within a subterranean zone. The propagation can depend on mechanical stresses in the reservoir and the fracture properties of the rocks, and certain rock formations can require a significant amount of energy to propagate fractures.

SUMMARY

The present disclosure describes technologies relating to increasing hydraulic fracturing efficiencies in subterranean zones by degrading organic matter, such as kerogen. In a general implementation, a method for treating kerogen in a subterranean zone includes placing a composition in the subterranean zone, and the composition includes an oxidizer including sodium bromate and an additive including a tetrasubstituted ammonium salt.

In an aspect combinable with the general implementation, the subterranean zone can include carbonate rock including organic matter.

In another aspect combinable with any one of the previous aspects, the method can include fracturing the subterranean zone, and the fracturing can occur before placing the composition in the subterranean zone, while placing the composition in the subterranean zone, after placing the composition in the subterranean zone, or combinations of these.

In another aspect combinable with any one of the previous aspects, the composition can include a friction reducer including polyacrylamide, a copolymer of acrylamide, or derivatives of these.

In another aspect combinable with any one of the previous aspects, the sodium bromate can have a concentration of about 0.00005 moles per liter (M) to about 4.00 M.

In another aspect combinable with any one of the previous aspects, the tetrasubstituted ammonium salt can be present at a concentration of about 0.001 weight percent (wt %) to about 20 wt %.

In another aspect combinable with any one of the previous aspects, the composition can include an aqueous liquid having a potential of hydrogen (pH) of about 4 to about 8.

In another aspect combinable with any one of the previous aspects, the aqueous liquid can include a water, a brine, or combinations of these.

In another aspect combinable with any one of the previous aspects, the aqueous liquid can include a drilling fluid, a fracturing fluid, a diverting fluid, a lost circulation treatment fluid, or combinations of these.

In another general implementation, a method for fracturing a subterranean zone penetrated by a wellbore includes treating kerogen in the subterranean zone with a composition and fracturing the subterranean zone. The composition includes an oxidizer including sodium bromate having a concentration of about 0.00005 M to about 4.00 M and an additive including a tetrasubstituted ammonium salt.

In an aspect combinable with the general implementation, the subterranean zone can include carbonate rock including kerogen.

In another aspect combinable with any one of the previous aspects, the fracturing can occur before treating kerogen in the subterranean zone, while treating kerogen in the subterranean zone, subsequent to treating kerogen in the subterranean zone, or combinations of these.

In another aspect combinable with any one of the previous aspects, the composition can include a friction reducer including or derived from polyacrylamide.

In another aspect combinable with any one of the previous aspects, the tetrasubstituted ammonium salt can be present at a concentration of about 0.001 wt % to about 20 wt %.

In another aspect combinable with any one of the previous aspects, the composition can include an aqueous liquid having a pH of about 4 to about 8, and the aqueous liquid can include a water, a brine, a drilling fluid, a fracturing fluid, a diverting fluid, a lost circulation treatment fluid, or combinations of these.

In another general implementation, a method for treating kerogen in a subterranean zone includes placing a composition in the subterranean zone, and the composition includes an oxidizer and a tetrasubstituted ammonium salt.

The details of one or more implementations of the subject matter of this specification are set forth in the accompanying drawings and the description. Other features, aspects, and advantages of the subject matter will become apparent from the description, the drawings, and the claims.

DETAILED DESCRIPTION

Figure 1:
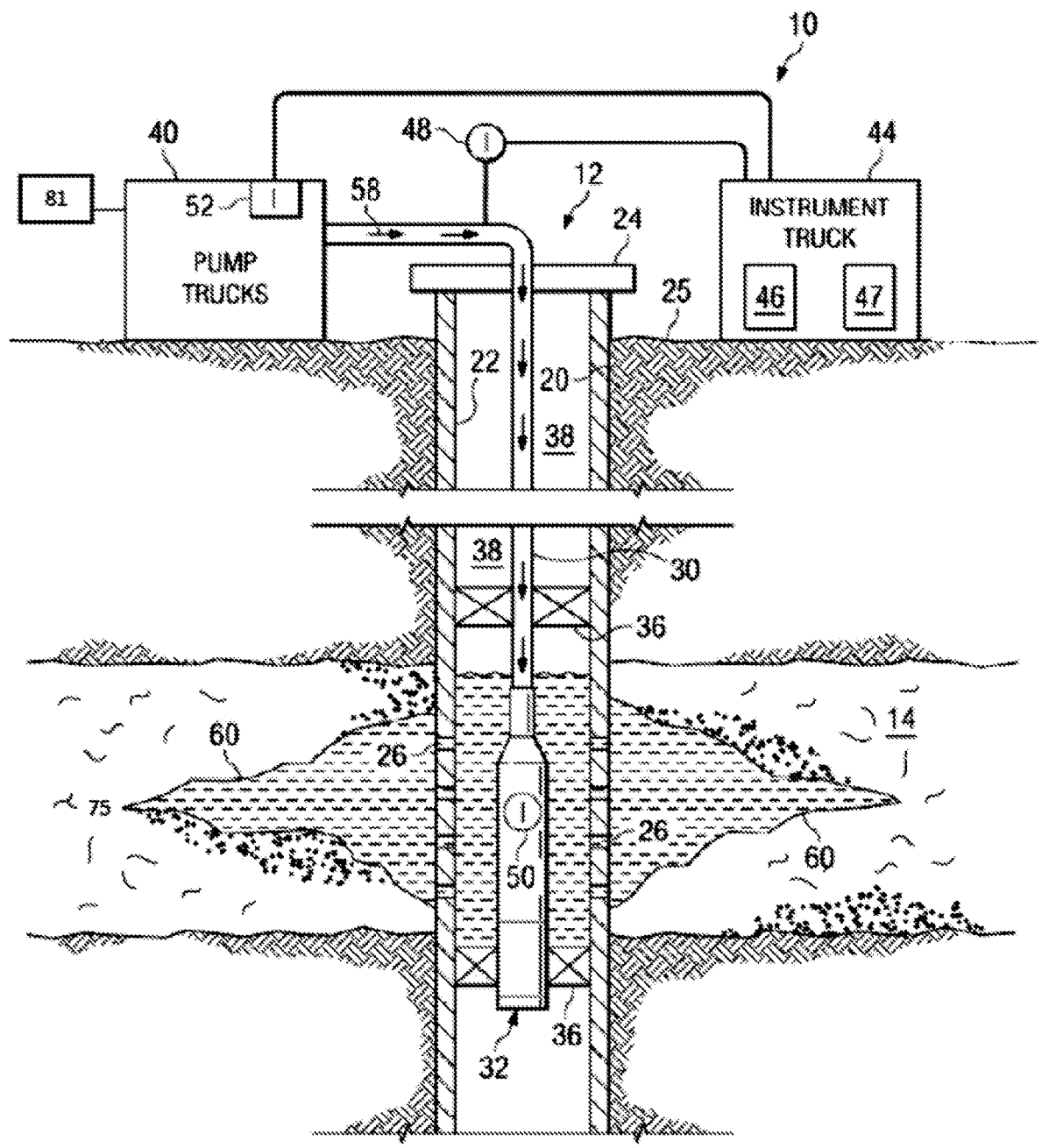
FIG. 1 is an example of a fracture treatment for a well.

This disclosure describes methods and compositions for degrading organic matter, such as kerogen, in a subterranean zone. Kerogen has a complex chemical structure and can characteristically vary depending on its type and maturity. It is known that this form of organic matter has elastomer characteristics with a polymeric nature. The origin and evolution of the kerogen can have a dramatic effect upon its structure including the ratio of aliphatic to aromatic carbon components and the presence of heteroatoms such as oxygen, nitrogen, or sulfur. These complex compositions and the increasing density of crosslinking that occurs in the structure during maturation can dictate the oil and gas potentials of the reservoir rock. The polymer structure of kerogen can give the source rock a tensile, elastic, ductile strength about 10 times more than the elastic strength of the granular source rock matrix.

The subject matter described in this specification can be implemented in particular implementations, so as to realize one or more of the following advantages. With certain embodiments of the methods and compositions provided in this document, hydraulic fracturing efficiencies in subterranean zones, such as organic-rich carbonate rock reservoirs, can be increased. Furthermore, fracture propagation, fracture length extension, and fracture width opening can be increased, and fracture re-healing and proppant embedment can be mitigated or prevented. By degrading viscoelastic and viscoplastic characteristics of the elastomer, rubber-like organic matter, such as kerogen, the potential of proppant embedment can be reduced. In some embodiments, reducing or degrading kerogen can also prevent the healing of the fracture and proppant embedment due to the viscoelastic and viscoplastic nature of polymers, in general, and kerogen, in particular. By degrading kerogen, the ductility of the rock matrix can be reduced, thereby requiring less energy to propagate fractures for hydraulic fracturing. By degrading kerogen, the permeability of the fractured and exposed formation can be improved (that is, increased), which can facilitate the flow of fluids through the formation. In other words, reducing or degrading the elastomeric characteristics of the kerogen can improve on the overall Stimulated Reservoir Volume (SRV) of the hydraulic fracturing operation, for the same input of energy from the pumps.

The term "about" as used in this disclosure can allow for a degree of variability in a value or range, for example, within 10%, within 5%, or within 1% of a stated value or of a stated limit of a range.

The term "substantially" as used in this disclosure refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "solvent" as used in this disclosure refers to a liquid that can dissolve a solid, another liquid, or a gas to form a solution. Non-limiting examples of solvents are silicones, organic compounds, water, alcohols, ionic liquids, and supercritical fluids.

The term "room temperature" as used in this disclosure refers to a temperature of about 15 degrees Celsius (° C.) to about 28° C.

The term "downhole" as used in this disclosure refers to under the surface of the earth, such as a location within or fluidly connected to a wellbore.

As used in this disclosure, the term "drilling fluid" refers to fluids, slurries, or muds used in drilling operations downhole, such as during the formation of the wellbore.

As used in this disclosure, the term "stimulation fluid" refers to fluids or slurries used downhole during stimulation activities of the well that can increase the production of a well, including perforation activities. In some examples, a stimulation fluid can include a fracturing fluid or an acidizing fluid.

As used in this disclosure, the term "clean-up fluid" refers to fluids or slurries used downhole during clean-up activities of the well, such as any treatment to remove material obstructing the flow of desired material from the subterranean zone. In one example, a clean-up fluid can be an acidification treatment to remove material formed by one or more perforation treatments. In another example, a clean-up fluid can be used to remove a filter cake.

As used in this disclosure, the term "fracturing fluid" refers to fluids or slurries used downhole during fracturing operations.

As used in this disclosure, the term "spotting fluid" refers to fluids or slurries used downhole during spotting operations, and can be any fluid designed for localized treatment of a downhole region. In one example, a spotting fluid can include a lost circulation material for treatment of a specific section of the wellbore, such as to seal off fractures in the wellbore and prevent sag. In another example, a spotting fluid can include a water control material. In some examples, a spotting fluid can be designed to free a stuck piece of drilling or extraction equipment, can reduce torque and drag with drilling lubricants, prevent differential sticking, promote wellbore stability, and can help to control mud weight.

As used in this disclosure, the term "completion fluid" refers to fluids or slurries used downhole during the completion phase of a well, including cementing compositions.

As used in this disclosure, the term "remedial treatment fluid" refers to fluids or slurries used downhole for remedial treatment of a well. Remedial treatments can include treatments designed to increase or maintain the production rate of a well, such as stimulation or clean-up treatments.

As used in this disclosure, the term "abandonment fluid" refers to fluids or slurries used downhole during or preceding the abandonment phase of a well.

As used in this disclosure, the term "acidizing fluid" refers to fluids or slurries used downhole during acidizing treatments. In one example, an acidizing fluid is used in a clean-up operation to remove material obstructing the flow of desired material, such as material formed during a perforation operation. In some examples, an acidizing fluid can be used for damage removal.

As used in this disclosure, the term "cementing fluid" refers to fluids or slurries used during cementing operations of a well. For example, a cementing fluid can include an aqueous mixture including at least one of cement and cement kiln dust. In another example, a cementing fluid can include a curable resinous material such as a polymer that is in an at least partially uncured state.

As used in this disclosure, the term "water control material" refers to a solid or liquid material that interacts with aqueous material downhole, such that hydrophobic material can more easily travel to the surface and such that hydrophilic material (including water) can less easily travel to the surface. A water control material can be used to treat a well to cause the proportion of water produced to decrease and to cause the proportion of hydrocarbons produced to increase, such as by selectively binding together material between water-producing subterranean zones and the wellbore while still allowing hydrocarbon-producing formations to maintain output.

As used in this disclosure, the term "packer fluid" refers to fluids or slurries that can be placed in the annular region of a well between tubing and outer casing uphole of a packer. In various examples, the packer fluid can provide hydrostatic pressure in order to decrease differential pressure across the sealing element, decrease differential pressure on the wellbore and casing to prevent collapse, and protect metals and elastomers from corrosion.

As used in this disclosure, the term "fluid" refers to liquids and gels, unless otherwise indicated.

As used in this disclosure, the term "subterranean material" or "subterranean zone" refers to any material under the surface of the earth, including under the surface of the bottom of the ocean. For example, a subterranean zone or material can be any section of a wellbore and any section of a subterranean petroleum- or water-producing formation or region in fluid contact with the wellbore. Placing a material in a subterranean zone can include contacting the material with any section of a wellbore or with any subterranean region in fluid contact the material. Subterranean materials can include any materials placed into the wellbore such as cement, drill shafts, liners, tubing, casing, or screens; placing a material in a subterranean zone can include contacting with such subterranean materials. In some examples, a subterranean zone or material can be any downhole region that can produce liquid or gaseous petroleum materials, water, or any downhole section in fluid contact with liquid or gaseous petroleum materials, or water. For example, a subterranean zone or material can be at least one of an area desired to be fractured, a fracture or an area surrounding a fracture, and a flow pathway or an area surrounding a flow pathway, in which a fracture or a flow pathway can be optionally fluidly connected to a subterranean petroleum- or water-producing region, directly or through one or more fractures or flow pathways.

As used in this disclosure, "treatment of a subterranean zone" can include any activity directed to extraction of water or petroleum materials from a subterranean petroleum- or water-producing formation or region, for example, including drilling, stimulation, hydraulic fracturing, clean-up, acidizing, completion, cementing, remedial treatment, abandonment, aquifer remediation, identifying oil rich regions via imaging techniques, and the like.

As used in this disclosure, a "flow pathway" downhole can include any suitable subterranean flow pathway through which two subterranean locations are in fluid connection. The flow pathway can be sufficient for petroleum or water to flow from one subterranean location to the wellbore or vice-versa. A flow pathway can include at least one of a hydraulic fracture, and a fluid connection across a screen, across gravel pack, across proppant, including across resin-bonded proppant or proppant deposited in a fracture, and across sand. A flow pathway can include a natural subterranean passageway through which fluids can flow. In some implementations, a flow pathway can be a water source and can include water. In some implementations, a flow pathway can be a petroleum source and can include petroleum. In some implementations, a flow pathway can be sufficient to divert water, a downhole fluid, or a produced hydrocarbon from a wellbore, fracture, or flow pathway connected to the pathway.

As used in this disclosure, "weight percent" (wt %) can be considered a mass fraction or a mass ratio of a substance to the total mixture or composition. Weight percent can be a weight-to-weight ratio or mass-to-mass ratio, unless indicated otherwise.

FIG. 1 illustrates an example of a fracture treatment 10 for a well 12. The well 12 can be in a wellbore 20 formed in a subterranean zone 14. The subterranean zone 14 can include, for example, a formation, a portion of a formation, or multiple formations in a hydrocarbon-bearing reservoir from which recovery operations can be practiced to recover trapped hydrocarbons. Examples of unconventional hydrocarbon-bearing reservoirs include tight-gas sands, gas and oil shales, coalbed methane, heavy oil and tar sands, and gas-hydrate deposits. In some implementations, the subterranean zone 14 includes an underground formation of naturally fractured rock containing hydrocarbons (for example, oil, gas, or both). For example, the subterranean zone 14 can include a fractured shale. In some implementations, the well 12 can intersect other suitable types of formations, including reservoirs that are not naturally fractured in any significant amount.

The well 12 can include a casing 22 and well head 24. The wellbore 20 can be a vertical, horizontal, deviated, or multilateral bore. The casing 22 can be cemented or otherwise suitably secured in the well bore 20. Perforations 26 can be formed in the casing 22 at the level of the subterranean zone 14 to allow oil, gas, and by-products to flow into the well 12 and be produced to the surface 25. Perforations 26 can be formed using shape charges, a perforating gun or otherwise.

For the fracture treatment 10, a work string 30 can be disposed in the well bore 20. The work string 30 can be coiled tubing, sectioned pipe or other suitable tubing. A fracturing tool 32 can be coupled to an end of the work string 30. Packers 36 can seal an annulus 38 of the well bore 20 uphole of and down hole of the subterranean zone 14. Packers 36 can be mechanical, fluid inflatable or other suitable packers.

One or more pump trucks 40 can be coupled to the work string 30 at the surface 25. The pump trucks 40 pump fracture fluid 58 down the work string 30 to perform the fracture treatment 10 and generate the fracture 60. The fracture fluid 58 can include a fluid pad, proppants, flush fluid, or a combination of these components. The pump trucks 40 can include mobile vehicles, equipment such as skids or other suitable structures.

One or more instrument trucks 44 can also be provided at the surface 25. The instrument truck 44 can include a fracture control system 46 and a fracture simulator 47. The fracture control system 46 monitors and controls the fracture treatment 10. The fracture control system 46 can control the pump trucks 40 and fluid valves to stop and start the fracture treatment 10 as well as to stop and start the pad phase, proppant phase, and flush phase of the fracture treatment 10. The fracture control system 46 communicates with surface and subsurface instruments to monitor and control the fracture treatment 10. In some implementations, the surface and subsurface instruments include surface sensors 48, down-hole sensors 50 and pump controls 52.

A quantity of energy applied by the fracture control system 46 to generate the fractures 60 in the subterranean zone 14 can be affected not only by the properties of the reservoir rock in the subterranean zone but also by the organic matter (for example, kerogen 75) intertwined within the rock matrix. As discussed within this disclosure, kerogen in a reservoir can increase the tensile strength of the rock, for example, by as much as 100-fold, resulting in a corresponding increase in the ultimate tensile strength of the rock. The modulus of toughness of the rock-kerogen combination compared to the rock alone can require a large quantity of energy to generate fractures in such a reservoir. Moreover, the presence of kerogen in the reservoir can affect production as well. For example, elastomeric kerogen can have rubber-like properties, which can prematurely close fractures resulting in decrease in production. Accordingly, the presence of kerogen in a subterranean zone can decrease an efficiency of hydraulic fracturing treatments.

This specification describes compositions 81 to degrade the kerogen encountered in subterranean zones, such as at the openings of cracks in hydraulic fractures. The compositions can include hydraulic fracturing fluids (for example, the fracture fluid 58) and flowed through the subterranean zone (for example, a reservoir). While the kerogen is degraded (or subsequent to the degradation of kerogen), a quantity of energy to generate and propagate fractures in the subterranean zone (for example, a reservoir) can decrease, thereby increasing an efficiency (for example, cost, time, and long-term effect) of the fracturing process. In addition, fracture length and formation surface exposure after wellbore shut-in can be greater than corresponding parameters in reservoirs in which the kerogen has not been degraded. In addition, at least partially removing the kerogen and other organic matter from the near fracture zone can decrease the propensity for the fractures to close (re-heal) after the pressure is released from pumping the fracturing, thereby improving the overall productivity of the well.

The compositions described in this disclosure can be used as a kerogen control material to break down, dissolve, or remove all or parts of the kerogen in or near the areas to be hydraulically fractured. Using the compositions described in this disclosure, the kerogen or other organic matter (or both) can be broken down. To do so, aqueous fluids which contain oxidizers can be pumped into the subterranean zone. For example, the compositions can include strong oxidizers including sodium bromate.

The byproducts of the reaction between the kerogen and the composition can dissipate as gases or can dissolve in an aqueous media of a fluid, such as a fracture fluid. The byproducts can then be removed from the formation during flowback of the fracturing fluid.

Figure 2:
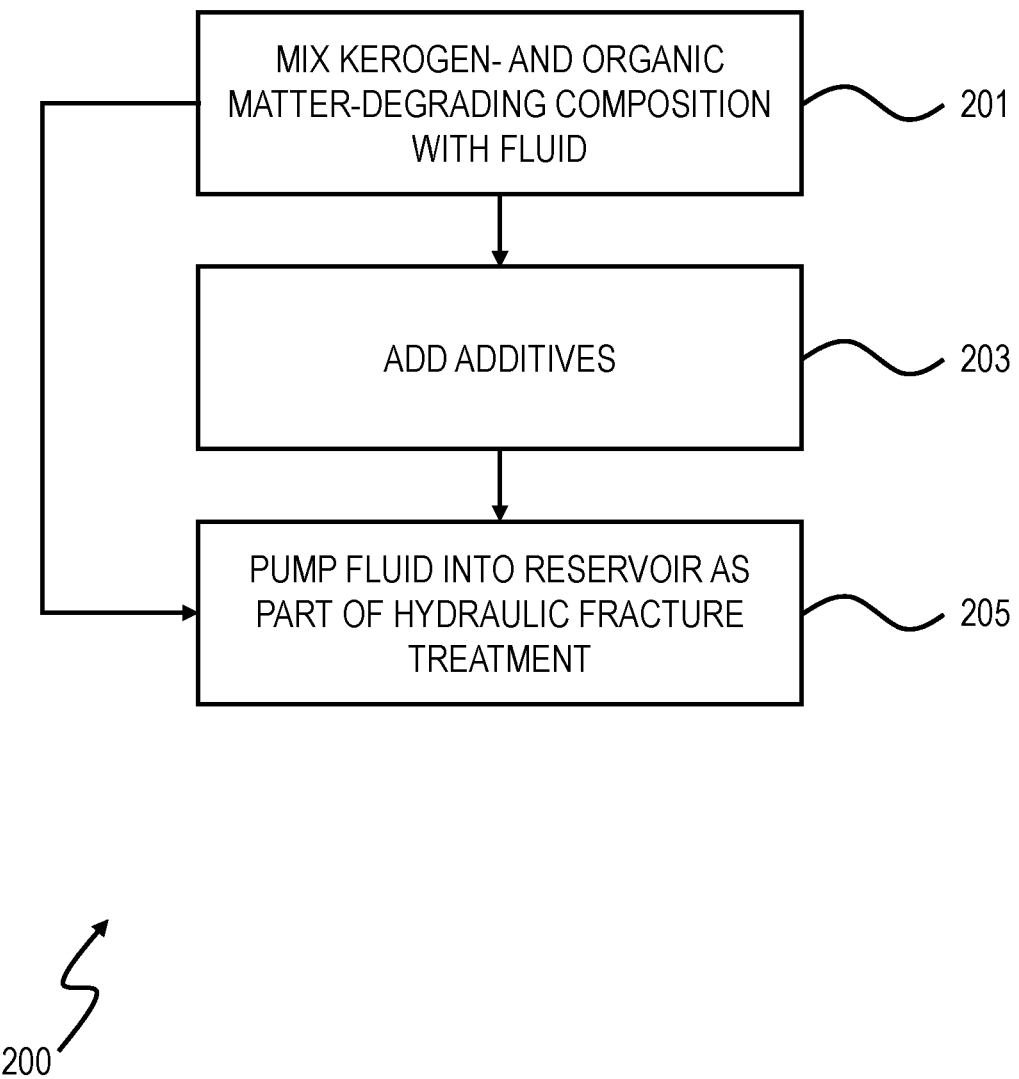
FIG. 2 is a flow chart of an example method for treating a well.

FIG. 2 is a flowchart of an example of a process 200 for degrading kerogen in a subterranean zone. At 201, a kerogen- and organic matter-degrading composition (for example, a composition including an oxidizer, such as sodium bromate) is mixed with a fluid. The fluid can be a hydraulic fracture fluid or a pad fluid that is flowed into the reservoir before the hydraulic fracture fluid (or both). At 205, the fluid (with the kerogen- and organic matter-degrading composition) is flowed into the reservoir as part of a hydraulic fracture treatment. As described previously, the kerogen and organic matter degrade upon reacting with the composition. At 203, an additive, such as friction reducer, can be added to the mixture of the composition and the fluid before pumping the fluid into the reservoir at 205. Other potential additives include any material that is compatible with the kerogen- and organic matter-degrading composition, for example, a tetrasubstituted ammonium salt that does not get oxidized by the sodium bromate in the subterranean zone.

The fluid (also referred as kerogen control fluid) can be delivered to a subterranean zone as a multi-pad fluid system, which can be delivered with hydraulic fracturing fluid sequences. The kerogen control fluid is configured to chemically react with the organic matter (such as kerogen) in the subterranean zone in order to break down and degrade the tensile nature of the organic matter, thereby degrading the viscoelastic properties of the hydraulic fracture faces and openings. A well can be shut in after delivery of the kerogen control fluid. The rate of reaction (that is, degradation) depends on the concentration of active ingredients (that is, kerogen control material, such as sodium bromate) and temperature. Greater concentrations of active ingredients and increased temperatures can increase the rate of degradation of the organic material, such as kerogen.

Further provided in this disclosure is a method of treating kerogen in a subterranean zone. The method can include placing in the subterranean zone a composition that includes an oxidizer. In some embodiments, the oxidizer can be a sodium bromate. Before introducing the composition to the subterranean zone, the oxidizer can have a concentration of about 0.00005 molar (M) to about 4.00 M. For example, the bromate can have a concentration of about 0.00005, 0.0005, 0.005, 0.05 M, 0.10 M, 0.20 M, 0.30 M, 0.40 M, 0.50 M, 0.75 M, 1.0 M, 1.25 M, 1.50 M, 2.0 M, 3.0 M, or about 4.0 M. In some implementations, the subterranean zone includes carbonate rock (for example, rock formations that include carbonate minerals).

The necessary concentration of the oxidizer in the composition can be determined based on the amount of fluid downhole at the time of placing the composition into the subterranean zone, as well as the amount and type of kerogen in the subterranean zone. Other factors that are relevant for determining the concentration of oxidizer required include the amount of pyrite or other iron sulfides in the subterranean zone as well as the amount of friction reducer, viscosifier or other organic component in the treatment fluid. Further, estimating the rock surface area within the fracture network with which the treatment fluid will make contact in the formation can be considered.

For example, the concentration of the oxidizer can be determined by performing at least one of the following: (i) performing laboratory tests on kerogen embedded in rock surfaces (for example, etching); (ii) estimating the expected size of the fracture network and the resulting surface area of the fractured zones; (iii) determine the weight percent of the total organic carbon (TOC) in the formation (for example, by using a TOC analyzer, pyrolysis unit, well log, or combinations of these); (iv) determining the weight percent of iron sulfide in the formation (for example by testing using either x-ray fluorescence, x-ray diffraction, energy dispersive x-ray spectroscopy, well log, or combinations of these); (v) determining the weight percent of friction reducer, viscosifier, and other organic materials in the treatment fluid; and (vi) determining the oxidizer concentration by accounting for the amount needed to degrade the kerogen while also accounting for the iron sulfide present and any organic materials present in the treatment fluid.

The composition can further include additives. In some implementations, the additive can be a tetrasubstituted ammonium salt. For example, the salt can be an ammonium salt such as chlorides or bromides of tetraalkylammonium, hexadecyltrimethylammonium, phenyltrimethylammonium, $C_{12}$-$C_{14}$-alkylbenzylammonium, quaternary ammonium, benzyltrialkylammonium, or combinations of these. The salt can be present at a concentration of about 0.001 wt % to about 30 wt % of the composition, about 0.001 wt % to about 25 wt %, about 0.001 wt % to about 20 wt %, about 0.001 wt % to about 15 wt %, or about 0.001 wt % to about 10 wt % of the composition. For example, the salt can be present at a concentration of about 2 wt % to about 7 wt %.

In some implementations, the composition further includes a friction reducer. A friction reducer can reduce friction forces experienced by material, tools, and tubulars in a wellbore. Friction reducer can be useful in cases where friction forces limit the passage of material along the wellbore. The friction reducer can include polyacrylamide or be derived from polyacrylamide.

In some implementations, the composition further includes an aqueous liquid. The aqueous liquid can include fresh water, a brine, a produced water, a flowback water, a brackish water, an Arab-D-brine, a sea water, or combinations of these. The aqueous liquid can include a drilling fluid, a fracturing fluid, a diverting fluid, a lost circulation treatment fluid, or combinations of these. The aqueous liquid can have a potential of hydrogen (pH) of about 4.0 to about 8.0. For example, the aqueous liquid can have a pH of about 5.0 to about 7.0.

The method can also include obtaining or providing the composition. Obtaining or providing the composition can occur above-surface or in the subterranean zone. The method can also further include combining the composition with an aqueous or oil-based fluid including a drilling fluid, stimulation fluid, fracturing fluid, spotting fluid, clean-up fluid, completion fluid, remedial treatment fluid, abandonment fluid, pill, acidizing fluid, cementing fluid, packer fluid, logging fluid, or combinations of these to form a mixture. Placing the composition in the subterranean zone includes placing the mixture in the subterranean zone.

The composition can also further include a saline, an aqueous base, an oil, an organic solvent, a synthetic fluid oil phase, an aqueous solution, an alcohol or polyol, a cellulose, a starch, an alkalinity control agent, an acidity control agent, a density control agent, a density modifier, an emulsifier, a dispersant, a polymeric stabilizer, a crosslinking agent, a polyacrylamide, a polymer or combination of polymers, an antioxidant, a heat stabilizer, a foam control agent, a diluent, a plasticizer, a filler or inorganic particle, a pigment, a dye, a precipitating agent, a rheology modifier, an oil-wetting agent, a set retarding additive, a surfactant, a corrosion inhibitor, a gas, a weight reducing additive, a heavy-weight additive, a lost circulation material, a filtration control additive, a salt, a fiber, a thixotropic additive, a breaker, a curing accelerator, a curing retarder, a pH modifier, chelating agent, a scale inhibitor, an enzyme, a resin, a water control material, an additional oxidizer, a marker, a Portland cement, pozzolana cement, a gypsum cement, a cement with alumina content, a slag cement, a silica cement, a fly ash, a metakaolin, a shale, a zeolite, a crystalline silica compound, an amorphous silica, a hydratable clay, a microsphere, a pozzolan lime, or combinations of these.

The method can further include fracturing the subterranean zone. In some implementations, the fracturing includes slickwater fracturing. The slickwater fracturing can employ an aqueous fluid to induce a subterranean fracture. The slickwater fluids can include a fresh water or a brine having sufficient friction reducing agents to minimize the tubular friction pressures.

In some implementations, at least one of prior to, during, and after the placing of the composition in the subterranean zone, the composition is used in the subterranean zone, at least one of alone or in combination with other materials, as a drilling fluid, stimulation fluid, fracturing fluid, spotting fluid, clean-up fluid, completion fluid, remedial treatment fluid, abandonment fluid, pill, acidizing fluid, cementing fluid, packer fluid, logging fluid, or combinations of these.

In some implementations the composition can be encapsulated and configured to be flowed into a subterranean zone. The encapsulated composition can be configured to be slow-released into the subterranean zone. Slow-releasing the composition into the reservoir rock can controllably delay contact between the reservoir rock and the composition to degrade the organic matter. The encapsulated composition can also be configured to break during fracture propagation or closure releasing the composition. In some implementations, the composition can be non-encapsulated and configured to be flowed into a subterranean zone. In some implementations, the composition can include a mixture of encapsulated and non-encapsulated material and configured to be flowed into a subterranean zone.

In some implementations, the composition can further include a clay stabilizer. A clay stabilizer is an additive that can prevent the migration or swelling of clay particles in reaction to water-base fluids (that is, a drilling fluid or mud in which water or saltwater is the major liquid phase phase, as well as the wetting or external phase). Without the presence clay stabilizer, some water-base fluids can affect the electrical charge of clay platelets in the subterranean zone, which can cause the platelets to swell or migrate in the flowing fluid and, once dispersed, can plug areas of the subterranean zone. Clay stabilizers can retain clay platelets in position by controlling the charge and electrolytic characteristics of a well treatment fluid. The clay stabilizer can include choline chloride, tetraalkylammonium chloride, a Group I chloride, or combinations of these. A Group I chloride is a compound which includes a chloride ion and a Group I element ion (also known as an alkali metal ion), such as potassium chloride or sodium chloride. The composition can further include a surfactant. A surfactant is an additive that preferentially adsorbs at an interface, thereby lowering the surface tension or interfacial tension between fluids or between a fluid and a solid. The surfactant can include hexadecyltrimethylammonium chloride, tallowamine quat, $C_{12}$-$C_{16}$ alkylammonium quat, or combinations of these. The composition can further include a biocide. A biocide is an additive that kills bacteria, so they are also referred as bactericides. Biocides can be used to control sulfate-reducing bacteria, slime-forming bacteria, iron-oxidizing bacteria, and bacteria that attacks polymers in fracturing fluids and recovery fluids. The biocide can include tetrakis(hydroxymethyl)phosphonium sulfate, $C_{12}$-$C_{14}$ alkylbenzylammonium chloride, benzyltrimethyl ammonium chloride, benzyltriethylammonium chloride, or combinations of these. Some specific examples of additives suitable for the composition include an aqueous solution of 60% benzyltrimethylammonium chloride (e.g., BTMAC-60 or 60% BTMAC), a solution of 85% $C_{12}$-$C_{14}$ alkyl dimethylbenzylammonium chloride in water and isopropanol (e.g., StarQuat™ T-85), an aqueous solution of 50% $C_{12}$-$C_{14}$ alkyl dimethylbenzylammonium chloride (e.g., StarQuat™ T-50), tallowamine diethylsulfate quat (e.g., StarQuat™ TAM 20 DQ), and an aqueous solution of benzyltriethylammonium chloride (e.g., StarQuat™ ESL Conc).

The compositions described in this disclosure can further include one or more suitable components. The additional components can be any components, such that the composition can be used as described in this disclosure.

In some implementations, the composition, or a mixture including the same, can include any suitable amount of any suitable material used in a downhole fluid. For example, the composition or a mixture including the same can include water, saline, aqueous base, acid, oil, organic solvent, synthetic fluid oil phase, aqueous solution, alcohol or polyol, cellulose, starch, alkalinity control agents, acidity control agents, density control agents, density modifiers, emulsifiers, dispersants, polymeric stabilizers, crosslinking agents, polyacrylamide, a polymer or combination of polymers, antioxidants, heat stabilizers, foam control agents, solvents, diluents, plasticizer, filler or inorganic particle, pigment, dye, precipitating agent, rheology modifier, oil-wetting agents, set retarding additives, surfactants, gases, weight reducing additives, heavy-weight additives, lost circulation materials, filtration control additives, fibers, thixotropic additives, breakers, crosslinkers, rheology modifiers, curing accelerators, curing retarders, pH modifiers, chelating agents, scale inhibitors, enzymes, resins, water control materials, oxidizers, markers, Portland cement, pozzolana cement, gypsum cement, cement with alumina content, slag cement, silica cement, fly ash, metakaolin, shale, zeolite, a crystalline silica compound, amorphous silica, hydratable clays, microspheres, lime, or combinations of these.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

In the methods of manufacturing described in this disclosure, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the process.

Example 1

Various kerogen control fluids were tested on kerogen-rich carbonate rock samples of wet gas and condensate maturity. Bitumen (a mixture of hydrocarbons in a viscous liquid or semi-solid form) was extracted from geological samples, and then the mineral (carbonate) matrix was digested with hydrofluoric and hydrochloric acids. The remaining kerogen (for Example 1, the kerogen is Type II-S with a hydrogen-carbon ratio of 0.612) was subjected to various kerogen control fluids. The kerogen control fluid included kerogen control material. The kerogen control material was the active ingredient that degraded the kerogen elastomer effects in the subterranean zone (for example, the sodium bromate oxidizer). In a few experiments, the kerogen control fluid included an additive. The following table shows results of various experiments demonstrating the degradation of kerogen with respect to time in the presence of a kerogen control fluid. The concentration of kerogen control material (KCM) in weight % in the following table is the initial kerogen content before degradation.

| Experiment number | Kerogen control material (KCM) | Concentration of KCM (weight %) | Kerogen degradation (%) | Temperature (° C.) | Time (hours) |
|---|---|---|---|---|---|
| 1 | Sodium bromate | 4 | 80 | 150 | 20 |
| 2 | Sodium bromate | 4 | 64 | 150 | 8 |
| 3 | Sodium bromate | 4 | 26 | 150 | 3 |
| 4 | Sodium bromate | 0.4 | 10 | 150 | 3 |
| 5 | Sodium bromate | 0.4 | 5.2 | 150 | 3 |
| 6 | Sodium bromate | 0.4 | 2.8 | 150 | 3 |

In the experiments for Example 1, the samples were exposed to fluids containing kerogen control materials at a temperature of 150° C. for at least 3 hours. The percent kerogen degradation shown in the table for Example 1 are the averages of three repeated tests for each experiment. Experiment #4 also included 0.05 weight % hexadecyltrimethylammonium chloride as an additive. Experiment #5 also included 0.05 weight % choline chloride as an additive. Experiment #6 also included 0.05 weight % tetramethylammonium chloride as an additive.

Example 2

The following table shows the composition of one example of a kerogen control fluid. The kerogen control fluid in Example 2 had a pH between about 6.0 and about 8.0 at room temperature and at 150° C. The compatibility of the additives with the kerogen control material was maintained to a pH of about 4.0. In the following table, the clay stabilizer is potassium chloride (KCl), the surfactant is hexadecyltrimethylammonium chloride, the kerogen control material 1 is sodium bromate, the kerogen control material 2 is encapsulated sodium bromate, and the biocide is benzyltriethylammonium chloride.

| Additive | Concentration (weight %) | Working range (weight %) |
|---|---|---|
| Clay stabilizer | 2% | 0.001%-10% |
| Surfactant | 0.025% | 0.001%-0.1% |
| Kerogen control material 1 | 0.06% | 0.01%-1% |
| Kerogen control material 2 | 0.09% | 0.01%-1% |
| Biocide | 0.0125% | 0.001%-0.1% |

The range of pH for the kerogen control fluid allows for reduced acid corrosivity. Three identical corrosion tests were performed, where the kerogen control fluid (whose composition is shown in the table for Example 2) was prepared in a glass tube, in which a carbon steel 1018 coupon with known mass was suspended. The glass tube was heated for 6 hours at 50° C. and then cooled to room temperature. The coupon was removed from the kerogen control fluid, cleaned, dried, and weighed in order to determine a loss of mass due to corrosion. The average corrosion loss for the three tests was determined to be 0.0004 pound per square foot ($lb/ft^2$), which is significantly less than the maximum allowable corrosion loss of 0.05 $lb/ft^2$.

Three additional corrosion tests were performed using kerogen control material without additives. A glass tube containing an aqueous solution of 0.12 weight % kerogen control material (sodium bromate) was prepared, in which a carbon steel 1018 coupon with known mass was suspended. The glass tube was heated for 6 hours at 50 C and then cooled to room temperature. The coupon was removed from the solution, cleaned, dried, and weighed in order to determine a loss of mass due to corrosion. The average corrosion loss for the three tests was determined to be 0.0007 $lb/ft^2$, which is significantly less than the maximum allowable corrosion loss of 0.05 $lb/ft^2$.

While this specification contains many specific implementation details, these should not be construed as limitations on the scope of the subject matter or on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example implementations do not define or constrain this disclosure. Other changes, substitutions, and alterations are also possible without departing from the spirit and scope of this disclosure.

What is claimed is:

1. A method for treating kerogen in a subterranean zone, the method comprising:
   determining a concentration of oxidizer to include in a composition, wherein determining the concentration of oxidizer comprises:
      determining a weight percent of iron sulfide in the subterranean zone; and
      determining the concentration of oxidizer by accounting for an amount of oxidizer needed to degrade the kerogen and for the iron sulfide; and
   breaking down the kerogen in the subterranean zone using the composition comprising:
   the determined concentration of the oxidizer, wherein the oxidizer comprises sodium bromate; and
   an additive comprising a tetrasubstituted ammonium salt selected from the group consisting of hexadecyltrimethylammonium salt, phenyltrimethylammonium salt, $C_{12}$-$C_{14}$-alkylbenzylammonium salt, and benzyltrialkyl ammonium salt, wherein the additive is not oxidized by the oxidizer in the subterranean zone.

2. The method of claim 1, wherein the subterranean zone comprises carbonate rock comprising organic matter.

3. The method of claim 1, further comprising fracturing the subterranean zone, wherein the fracturing occurs before breaking down the kerogen in the subterranean zone, while breaking down the kerogen in the subterranean zone, after breaking down the kerogen in the subterranean zone, or combinations thereof.

4. The method of claim 1, wherein the composition further comprises a friction reducer comprising polyacrylamide, a copolymer of acrylamide, or derivatives thereof.

5. The method of claim 1, wherein the sodium bromate has a concentration of about 0.00005 moles per liter (M) to about 4.00 M.

6. The method of claim 1, wherein the tetrasubstituted ammonium salt is present at a concentration of about 0.001 weight percent (wt %) to about 20 wt %.

7. The method of claim 1, wherein the composition further comprises an aqueous liquid having a potential of hydrogen (pH) of about 4 to about 8.

8. The method of claim 7, wherein the aqueous liquid comprises a water, a brine, or combinations thereof.

9. The method of claim 1, further comprising placing the composition in the subterranean zone during drilling operations, during fracturing operations, during diverting operations, during lost circulation treatment, or combinations thereof.

10. A method for fracturing a subterranean zone penetrated by a wellbore, the method comprising:
    determining a concentration of oxidizer to include in a composition, wherein determining the concentration of oxidizer comprises:
       determining a weight percent of iron sulfide in the subterranean zone; and
       determining the concentration of oxidizer by accounting for the iron sulfide;
    at least partially degrading kerogen in the subterranean zone with the composition, the composition comprising:
       the determined concentration of the oxidizer, the oxidizer comprising sodium bromate, the concentration of the oxidizer in a range of about 0.1 moles per liter (M) to about 4.00 M; and
       an additive comprising a tetrasubstituted ammonium salt selected from the group consisting of hexadecyltrimethylammonium salt, phenyltrimethylammonium salt, $C_{12}$-$C_{14}$-alkylbenzylammonium salt, and benzyltrialkyl ammonium salt, wherein the additive is not oxidized by the oxidizer in the subterranean formation; and
    fracturing the subterranean zone.

11. The method of claim 10, wherein the subterranean zone comprises carbonate rock comprising kerogen.

12. The method of claim 10, wherein the fracturing occurs before at least partially degrading kerogen in the subterranean zone, while at least partially degrading kerogen in the subterranean zone, subsequent to at least partially degrading kerogen in the subterranean zone, or combinations thereof.

13. The method of claim 10, wherein the composition further comprises a friction reducer comprising or derived from polyacrylamide.

14. The method of claim 10, wherein the tetrasubstituted ammonium salt is present at a concentration of about 0.001 weight percent (wt %) to about 20 wt %.

15. The method of claim 10, wherein the composition further comprises an aqueous liquid having a potential of hydrogen (pH) of about 4 to about 8, and the method further comprises placing the composition in the subterranean zone during fracturing operations, during diverting operations, during lost circulation treatment, or combinations thereof.

16. The method of claim 10, wherein at least partially degrading the kerogen comprises degrading from about 2.8% up to about 80% of the kerogen in the subterranean zone.

* * * * *